United States Patent
Boston et al.

(10) Patent No.: US 6,392,562 B1
(45) Date of Patent: May 21, 2002

(54) FLUID PARTICLE SENSOR APPARATUS AND METHOD FOR TRANSMITTING DATA TO A REMOTE RECEIVER

(75) Inventors: Timothy A. Boston, Tremont; Rolland D. Scholl, Dunlap; Bruce E. Unger, Peoria, all of IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 09/221,400

(22) Filed: Dec. 28, 1998

(51) Int. Cl.⁷ .............................................. G08C 17/00
(52) U.S. Cl. ............ 340/870.28; 340/631; 340/870.16; 324/204; 73/61.41; 73/61.42
(58) Field of Search ......................... 340/870, 28, 631, 340/870.16; 324/204; 73/61.41, 61.42

(56) References Cited

U.S. PATENT DOCUMENTS

| | | | |
|---|---|---|---|
| 3,762,214 A | * 10/1973 | Bogusz | 73/61.41 |
| 4,219,805 A | * 8/1980 | Magee et al. | 340/631 |
| 5,335,540 A | 8/1994 | Bowler et al. | 73/146.5 |
| 5,446,452 A | 8/1995 | Litton | 340/870.17 |
| 5,461,385 A | 10/1995 | Armstrong | 342/42 |
| 5,483,827 A | 1/1996 | Kulka et al. | 73/146.5 |
| 5,502,378 A | 3/1996 | Atteberry et al. | 324/204 |
| 5,517,427 A | * 5/1996 | Joyce | 340/631 |
| 5,608,315 A | 3/1997 | Crayton et al. | 324/204 |
| 5,608,316 A | 3/1997 | Crayton et al. | 324/204 |
| 5,708,198 A | * 1/1998 | Fitch et al. | 73/61.42 |
| 5,728,933 A | 3/1998 | Schultz et al. | 73/146.5 |
| 5,731,754 A | 3/1998 | Lee, Jr. et al. | 340/447 |
| 6,297,626 B1 | * 10/2001 | Boston et al. | 324/204 |

* cited by examiner

Primary Examiner—Timothy Edwards

(57) ABSTRACT

A sensor for detecting particles in a fluid including a housing having a cavity associated therewith, a magnet disposed adjacent the cavity to attract particles into the cavity, first and second coils wound around the outer surface of the cavity, the induction of the first coil being responsive to the particle accumulation within the cavity, the inductance of the second coil being responsive to the temperature of the fluid and being independent of the particle accumulation within the cavity, a first microprocessor coupled to the first and second coils for processing the signals received therefrom and for outputting signals indicative of the particle accumulation within the cavity, an rf transmitter for converting the signals received from the first microprocessor into rf signals, and an rf antenna for transmitting the processed signals to a remote location. The signals outputted from the first microprocessor are encoded with an identification code to identify and distinguish such signals. A second rf antenna and receiver are positioned at a remote location for receiving the transmitted rf signals. The receiver decodes and processes such transmitted rf signals back into an electrical signal indicative of the particle accumulation within the cavity and inputs such signal into a second microprocessor or electronic controller which stores and monitors such information for diagnostic, prognostic and trend analysis purposes.

25 Claims, 5 Drawing Sheets

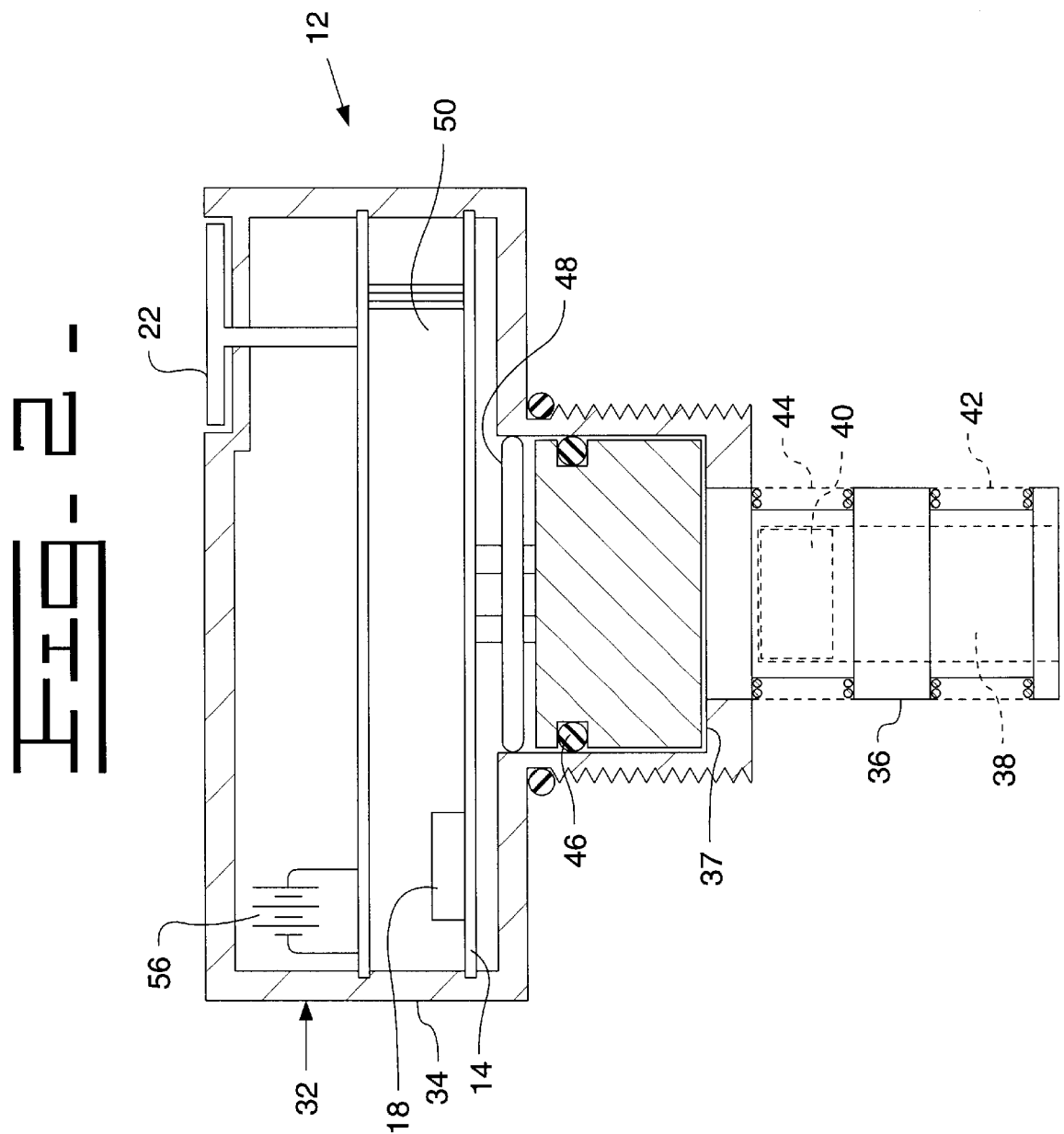

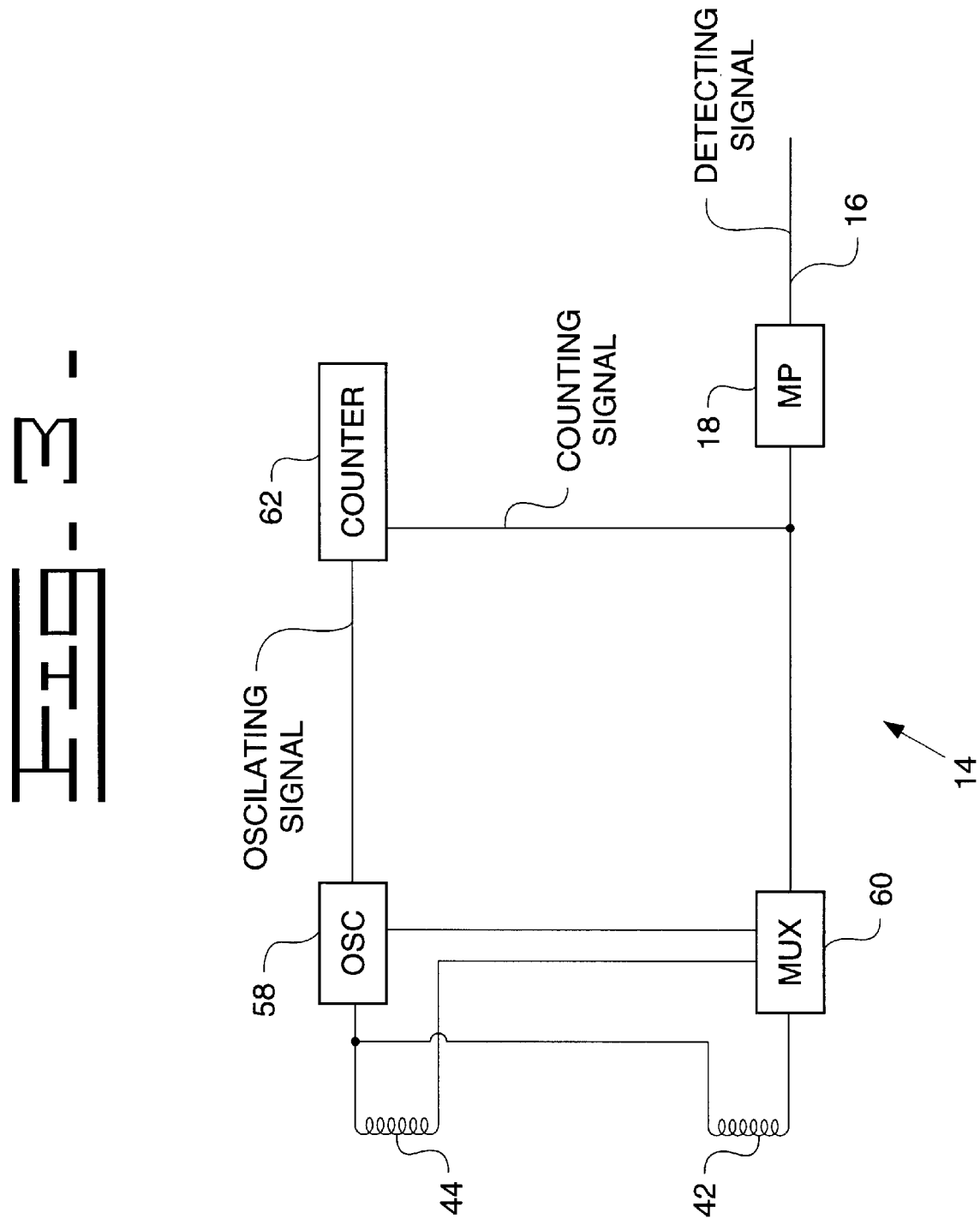

Fig_4_
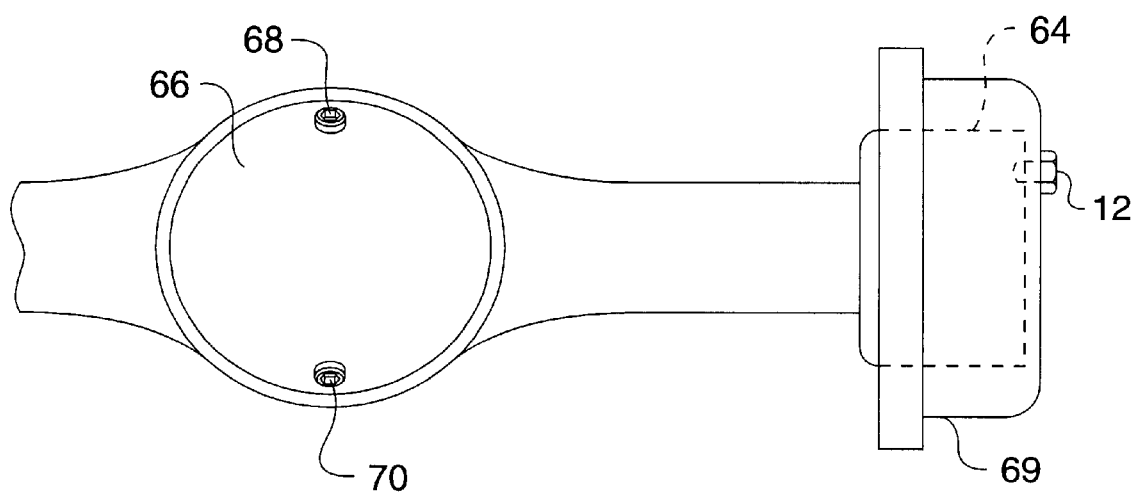

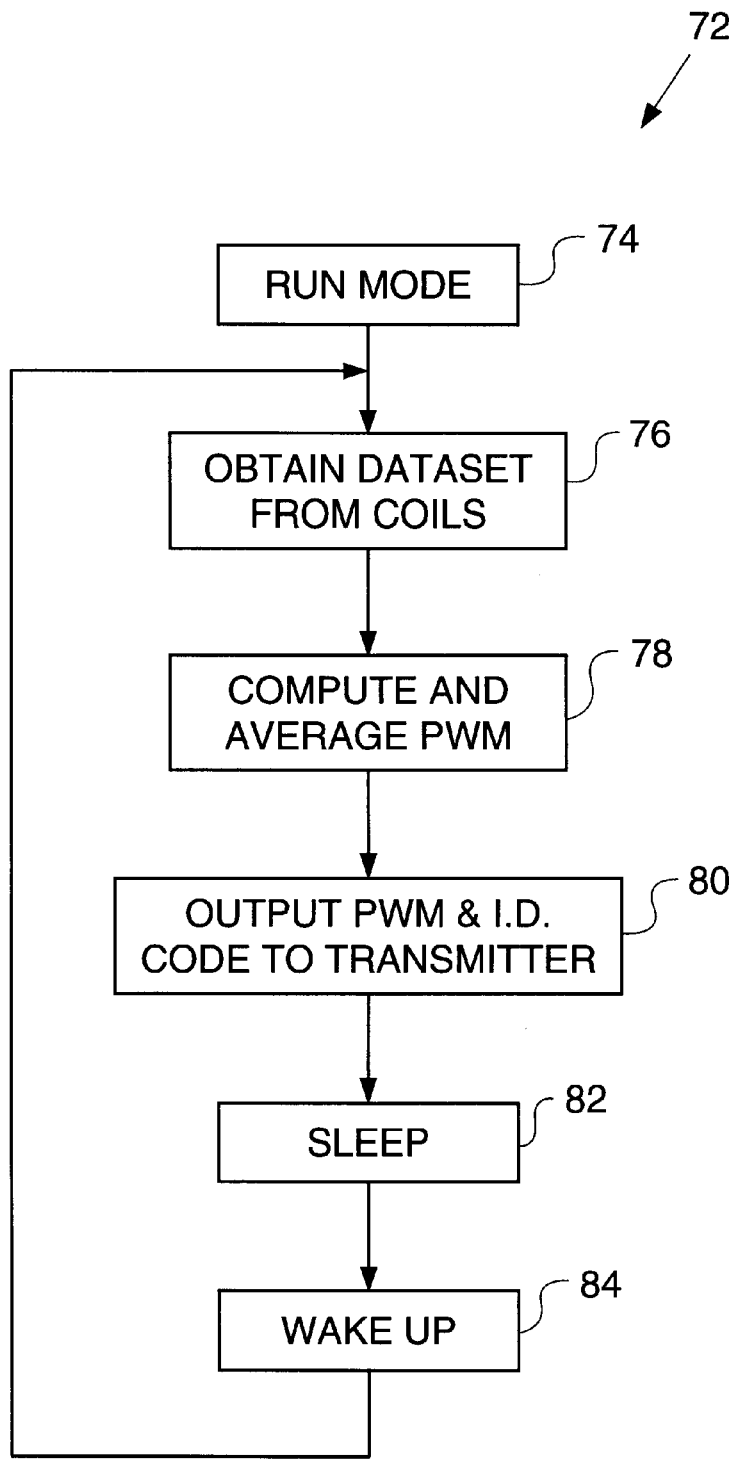

US 6,392,562 B1

FLUID PARTICLE SENSOR APPARATUS AND METHOD FOR TRANSMITTING DATA TO A REMOTE RECEIVER

TECHNICAL FIELD

This invention relates generally to an apparatus for detecting particles in a fluid medium and, more particularly, to an apparatus and method for detecting the presence of metallic particles in a fluid medium and transmitting data relating to the particle accumulation to a remote receiver.

BACKGROUND ART

Mechanical systems such as engines and transmissions utilize a lubricating oil or other fluid to dissipate heat within the system and to reduce wear on system components. However, due to the nature of the systems, wear does occur, resulting in the presence of small metallic particles in the oil or other lubricating fluid.

Due to the normal wear and the natural breakdown of the oil or other lubricating fluid, the lubricating fluid in such systems must be changed periodically. This is typically done on a time or usage basis, for example, every 90 days or 2000 hours of use. While small metal particles may result from normal wear, larger particles are usually an indication of abnormal wear or a more serious problem. For example, the resulting wear creates abnormal amounts of metal particles within the lubricant. Under normal maintenance procedures, the metal particles would be present in the lubricant for an extended period of time. If this condition is not identified and the appropriate repairs completed, more expensive repairs including the replacement of major system components may result.

Detection of metallic particles in hydraulic systems is equally important as hydraulic systems represent large expenses in the event of component failure. If failures are detected early, repair expenses can be minimized; however, if catastrophic failure occurs, the large amounts of particles caused by the failure can enter the hydraulic system and cause damage to many other components. Fortunately, any catastrophic failure of one of the components is often preceded by the gradual breakup of one or more components. If this breakup can be detected, corrective action can be taken before any further damage to surrounding components occurs.

In U.S. Pat. No. 5,502,378 assigned to the assignee of the present application, a sensor is disclosed that detects particles within a fluid that is generally comprised of a housing defining a cavity and a magnet disposed adjacent to the cavity bottom to attract particles into the cavity. A first coil is wound about the surface of the cavity. The induction of the first coil is responsive to the particle accumulation within the cavity. A second coil is wound about the magnet. The induction of the second coil is responsive to the temperature of the fluid and is independent of the particle accumulation within the cavity. In this system, electrical wiring connects the sensor to remote displays or alarms located in the operator compartment. In mechanical systems such as engines, transmissions, differentials, torque converters, oil and hydraulic systems, and other similar systems associated with work machines such as earth moving equipment, articulated trucks and so forth the wiring connecting the sensor to the warning or monitoring system may be subject and/or exposed to weather, extreme temperatures, and physical damage.

It would therefore be desirable if there were provided a fluid particle sensor that would transmit sensor data to the operator compartment or to a remote location without using conventional wiring for traversing the entire distance between the sensor and the monitoring or warning system; that would provide easier maintenance and installation; and that would provide trend data on the life of a particular machine system.

Accordingly, the present invention is directed to overcoming one or more of the problems as set forth above.

DISCLOSURE OF THE INVENTION

In one aspect of the present invention, a sensor for detecting particles in a fluid is generally comprised of a housing which houses the various components of the sensor, a battery for supplying power to such components, a microprocessor for processing incoming and outgoing signals, an rf transmitter for converting electrical signals into rf signals, and a first rf antenna for transmitting the processed signals to a remote location. The present sensor has a specific identification code associated therewith to identify and distinguish the signals outputted from such sensor. The identification code could also be tied to the particular type of equipment such as a particular work machine.

The sensor housing further includes a cavity having a magnet disposed adjacent to the cavity bottom to attract particles into the cavity. A first coil is wound around the outer surface of the cavity. The induction of the first coil is responsive to the particle accumulation within the cavity. A second coil is likewise wound about the outer surface of the cavity and is spaced from the first coil. The induction of the second coil is responsive to the temperature of the fluid and is independent of the particle accumulation within the cavity.

A second rf antenna and receiver positioned at a remote location receives the transmitted rf signals and decodes and processes such signals back into electrical signals indicative of the particle accumulation within the cavity for inputting into a second microprocessor or electronic controller. The second microprocessor stores and monitors the particle information generated by the present sensor and such information may be used for trend or component failure analysis. This particle information may also be inputted into a machine information monitoring system via a signal outputted by the second microprocessor, the monitoring system producing a warning signal in response thereto if such signal exceeds a predetermined value.

BRIEF DESCRIPTION OF THE DRAWINGS

For a better understanding of the present invention, reference may be made to the accompanying drawings in which:

FIG. 2 is a partial, cutaway view of the sensor housing incorporating the principles of the present invention;

FIG. 3 is a block diagram of the electrical circuitry associated with the fluid particle sensor shown in FIG. 1;

FIG. 4 is an illustration of a final drive assembly of a work machine with the fluid particle sensor mounted thereto; and FIG. 5 is a flow chart illustrating the run mode of the present fluid particle sensor.

BEST MODE FOR CARRYING OUT THE INVENTION

Figure 1:
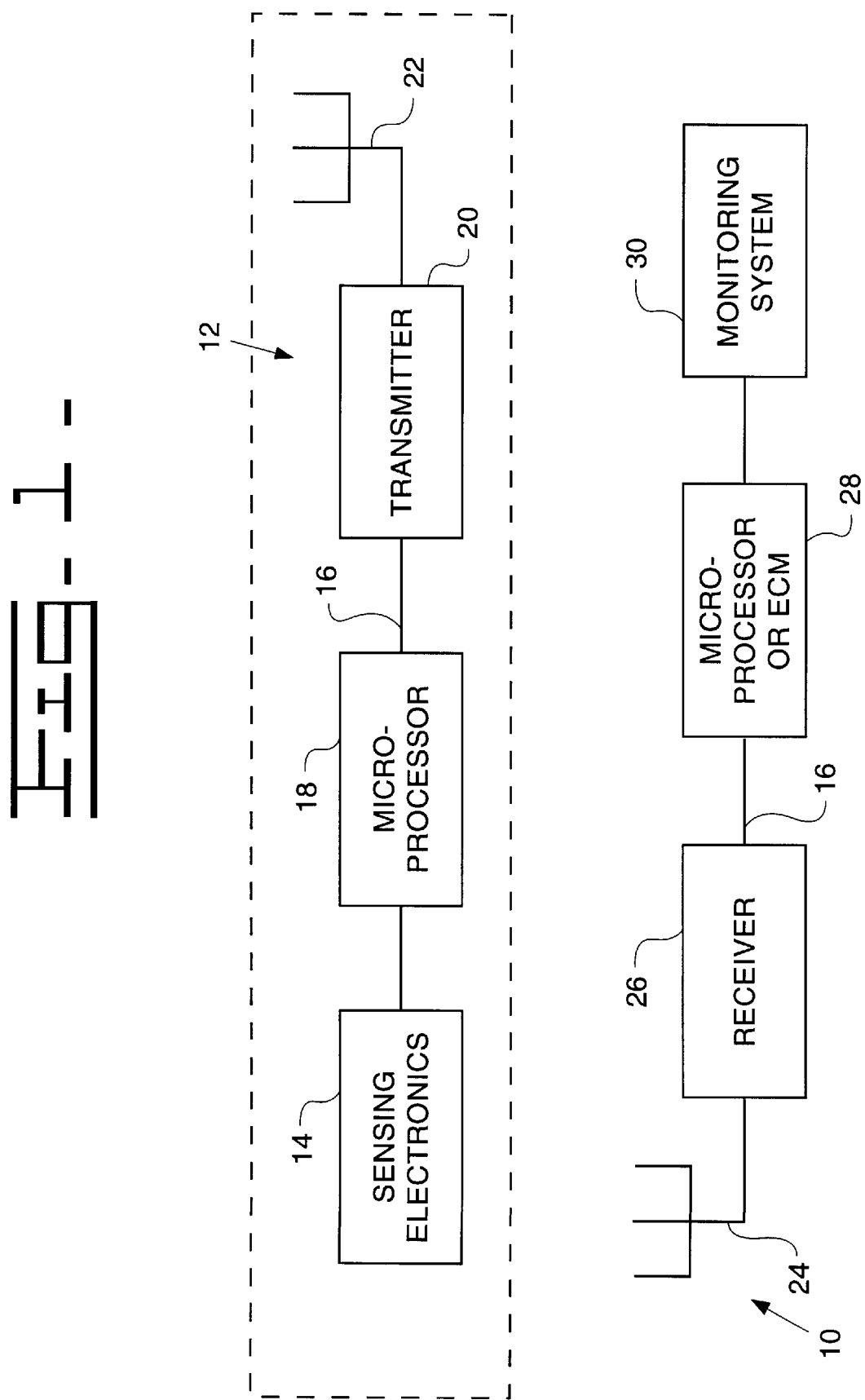
FIG. 1 is a block diagram of a fluid particle sensing system incorporating the principles of the present invention.

Referring to FIG. 1, there is shown a block diagram of a fluid particle sensing system 10 that incorporates the principles of the present invention. The present system 10 is comprised of a particle chip detector or sensor 12 as well as other components for transmitting data to a remote receiver. The chip detector 12 is adapted to detect particle accumulation within a fluid system such as within the transmission fluid of a final drive assembly associated with a differential on a particular work machine. The particular construction of the particle chip detector 12 will be discussed in more detail hereinafter. It should be noted, however, that the use of the present invention in association with a final drive assembly is for discussion purposes only and is not limited to such. The present invention may be adapted, for example, for use in engine oil pans, transmissions, differentials, torque converters, hydraulic systems, and other similar systems.

The present system 10 further includes sensing electronics 14 which produce a counting signal that is inputted into a first microprocessor 18. The microprocessor 18 is adapted to receive and amplify the counting signal and responsively produce a detection signal 16 which is representative of the amount of particle accumulation in a particular fluid system. The microprocessor 18 also encodes the detection signal 16 with an identifying code unique to the sensor 12 and inputs such encoded signal into an rf transmitter 20. The transmitter 20 then processes the electrical signal 16 into an rf signal and transmits the same via the antenna 22. As used herein, the term "electrical signal" is meant to include both an analogue type signal as well as a digital type signal, but not an rf signal.

A receiving antenna 24 located at a remote location receives the transmitted signal from antenna 22 and inputs such signal into the rf receiver 26 where the identifying information is decoded and the rf signal is converted back to an electrical signal, that is, either an analogue or a digital type signal. This converted signal is again indicative of the particle accumulation within the fluid and such signal is inputted into a second microprocessor or electronic controller 28 which stores and monitors the particular accumulation data or information for diagnostic, prognostic and trend analysis purposes. For example, such information may be used in diagnosing or predicting a component or system failure, or such data, when stored over time, may be used as historical data for conducting maintenance on the work machine. The microprocessor 28 may also output appropriate signals to a monitoring system 30 which may provide a warning signal to the operator in the operator compartment of the work machine representative of the particle accumulation being above a predetermined value. The monitoring system 30 may also be a remote CPU that stores trend and historical data on the maintenance of the machine.

The particle chip detector or sensor 12 may be of the type disclosed in U.S. Pat. No. 5,502,378 and assigned to the assignee of the present application, the construction and operation of which is incorporated herein by reference. Referring to FIG. 2, the sensor 12 includes a housing 32 which, in the particular embodiment illustrated in FIG. 2, is comprised of members 34 and 36, member 36 being insertably positioned within member 34 so as to engage and rest upon the edges or lip portion 37 of member 34. The member 34 is constructed so as to house various components of the sensor 12 as will be hereinafter further explained such as the sensing electronics 14, the microprocessor 18, the rf transmitter 20, the antenna 22, and the battery 56 as shown in FIG. 2. The member 36 is insertable through a suitable access opening (not shown) in the top portion of member 34 and includes a particle collection cavity 38 which is positioned adjacent to or at least partially extends into the fluid to be monitored. The cavity 38 is used for capturing and holding metallic particles present within the fluid and is positioned within member 34 as illustrated in FIG. 2 such that the cavity portion 38 is oriented as shown. At least the cavity portion 38 of member 36 should be made of a non-conducting material. It is recognized and anticipated that members 34 and 36 could be integrally formed such that housing 32 would be a one-piece unit. Other configurations of the sensor housing 32 are likewise possible and anticipated.

A magnet 40 is disposed adjacent to the bottom surface of the cavity 38. The magnet 40 attracts and contains the particles within the cavity 38. A first coil 42 is wound to form a helix about the proximity of the cavity 38. Accordingly, the induction of the first coil 42 is responsive to the particles that are accumulated within the cavity 38.

Though the inductance of the first coil 42 is relatively constant in the absence of accumulated particles, the inductance can change due to changes in the temperature of the fluid. A second coil 44 is therefore provided to compensate for the changing temperature of the fluid. The second coil 44 is arranged such that only the fluid temperature affects its inductance, and such inductance is not affected by the particles accumulated within the cavity 38. The second coil 44 is likewise wound in the form of a helix, and is spaced apart from the first coil 42 as shown in FIG. 2. The inductance of the second coil 44, therefore, is used as a baseline for determining the presence of particles within the cavity.

The sensor 12 further includes a microprocessor 18 and other sensing electronics 14, an rf transmitter 20 for receiving the detecting signal 16 from microprocessor 18, and an antenna 22 for transmitting the rf signal to the remote antenna 24 and receiver 26, all of which components 18, 20 and 22 are likewise mounted within and/or coupled to the housing member 34 as best shown in FIG. 2. A battery 56 provides power to the various sensor components. In this regard, the member 36 is mounted within the member 34 with a suitable O-ring 46 and a suitable press ring 48 to seal the section 50 of the member 34 which contains the electronics from the fluid. The O-ring 46 prevents fluid from entering into the electronics area of member 34 and the press ring 48 holds the member 36 in proper position and prevents such member from moving into the electronics area of member 34.

Referring now to FIG. 3, the electronic circuitry for the chip detector or sensor 12 is shown. The sensing electronics 14 is comprised of an oscillator 58 provided to energize both the first and second coils 42 and 44. The oscillator 58 includes a timer that energizes the coils with an oscillating waveform. A multiplexer 60 is provided to allow only one coil to energize at a given time. Consequently, the frequency of the oscillating waveform will be directly related to the inductance of the coil energized. A counter 62 is provided to tally the number of pulses associated with the oscillating waveform. For example, the oscillator 58 will energize one coil, while the counter 62 tallies the number of pulses of the oscillating waveform associated with the one coil. Once the number of pulses reaches a predetermined number, the counter 62 will reset. Responsively, the multiplexer 60 causes the other coil to energize. Meanwhile, the counter 62 tallies the number of pulses of the oscillating waveform associated with the other coil.

The counter 62 additionally produces a counting signal. The counting signal may be a continuous pulse width modulated (PWM) signal wherein the duration of the high pulse level is responsive to one coil being energized, for example, the first coil 42, while the low pulse level is responsive to the other coil being energized, for example, the second coil 44. The counting signal is delivered to the microprocessor 18 which produces a detecting signal 16 having a duty cycle that is responsive to the duty cycle of the counting signal in order to provide greater resolution. For example, a counting signal having a duty cycle of 50% may correspond to the microprocessor producing a detecting signal having a duty cycle of 5%, which is indicative of no particle accumulation in cavity 38. Meanwhile a counting signal having a duty cycle of 55% may correspond to a detecting signal having a duty cycle of 95%, which is indicative of a very large particle or a substantial amount of particle accumulation in cavity 38. It is recognized that other types of signals may likewise be used for the counting signal and the microprocessor 18 can be adapted to receive such different types of signals and produce a detecting signal in response thereto.

When a metallic particle enters cavity 38, the energized coil 42, in accordance with well known theory, introduces eddy currents in the particle. The eddy currents are a function, among other properties, of material conductivity. Thus, when a metallic particle enters cavity 38, eddy currents in the particle cause the effective inductance of the first coil 42 to decrease. Consequently, the oscillator 58 will produce the oscillating waveform with an increased frequency. Because eddy currents are a function of material conductivity, the greater the size of a particle or the greater the amount of particle accumulation within the cavity, the greater the change in the oscillating waveform frequency. In other words, the change in frequency of the oscillating waveform is due to the eddy current inductive effects on the metallic particles. It is recognized that the circuit shown in FIG. 3 is exemplary, and the manner of design and construction of this circuit, or a similar circuit, would be commonly known to a person skilled in the art.

Referring now to FIG. 4, the sensor 12 is shown mounted in the final drive transmission cavity 64 associated with a particular work machine such as an on or off highway truck. FIG. 4 also shows a differential assembly 66 which includes an oil fill aperture 68 and an oil drain aperture 70. The sensor 12 is typically mounted on the exterior of wheel or tire hub 69 such that the cavity 38 of sensor 12 extends through an opening (not shown) in the hub so as to at least partially extend into the final drive cavity 64. This arrangement provides for easy installation and easy serviceability of the sensor 12. This arrangement is but one method for allowing the sensor 12 to be positioned in the final drive cavity 64. Other means and connections for positioning the sensor 12 where desired in a particular fluid system such as in the final drive cavity 64 illustrated in FIG. 4 are also possible and anticipated.

Referring to FIG. 5, a flow chart 72 illustrates the run mode operation of the sensor 12. At predetermined time periods, the sensor 12 will be activated to both collect the particle accumulation data and thereafter transmit the same to the remote receiver 26. This activation typically takes place by programming the microprocessor 18, through the various timers associated therewith, to send a wake-up message to the sensing electronics 14 at predetermined time intervals, such as every 15 minutes. Upon wake-up, the sensing electronics 14 will acknowledge the message sent by the microprocessor 18 and initiate the run mode at step 74 of flow chart 72. At step 76, the sensor 12 will collect the particle accumulation information from the data collection coils 42 and 44 by energizing the same. The data set information collected at step 76 will typically include obtaining 64 different readings from the coils 42 and 44 and thereafter taking an average of the same. It is recognized and anticipated that any number of data set points may be taken from the coils 42 and 44 at step 76, depending upon the particular application involved. At step 78, the microprocessor 18 computes and averages the pulse width modulated data signals from the data set points obtained at step 76. This average pulse width modulated signal is thereafter outputted to the transmitter 20 at step 80 where such signal is converted into an rf signal for transmission through the antenna 22. The specific identification code for sensor 12 is likewise outputted to the transmitter 20 for conversion and transmission to the remote receiver 26. Once the particle accumulation data is transmitted via transmitter 20 and antenna 22 to the remote receiver 26, the sensor 12 goes into a sleep mode at step 82 until the sensing electronics 14 are again awakened, based upon the predetermined time interval, by the microprocessor 18 at step 84. Once awakened, sensor 12 will repeat operating steps 76–82 of flow chart 72 (FIG. 5) until it is again awakened at step 84.

Each time the sensor 12 outputs data via transmitter 20 to the remote receiver 26, such information is decoded and processed back into an electrical signal by the receiver 26 for inputting into the microprocessor 28. The microprocessor 28 will read and store the particle information generated by the sensor 12 and utilize such information for trend or component failure analysis. In addition, microprocessor 28 may further deliver a signal to some type of warning system such as the monitoring system 30 illustrated in FIG. 1. The monitoring system 30 may then provide a warning signal to the machine operator in response to the signal produced by microprocessor 28 being above a predetermined value. If such signal is greater than some predetermined value, the warning signal may activate some type of visual and/or audio warning signal in the operator compartment of the work machine thereby informing the operator of the warning condition.

INDUSTRIAL APPLICABILITY

With reference to the drawings and its operation, the present sensor system 10 is adapted to detect the accumulation of metal particles within a fluid. The sensor 12 has a transmitter and antenna to send information about particle accumulation within the fluid to a remote receiving unit. The present sensor system 10 is particularly well suited to detect metal particles within the lubricating fluid associated with various systems and components on a particular work machine, for example, within the machine's transmission system, the engine oil pan system, the hydraulic system, or the final drive system as illustrated herein. For example, the present sensor 12 could be located in a case drain line of a hydraulic pump or motor. As components such as the gears associated with a final drive assembly wear, tiny particles of metallic material such as iron, copper, brass and steel become suspended in the fluid. If one of the components in the particular fluid system becomes excessively worn out and/or is about to fail, the amount of particles suspended in the fluid increases substantially. Likewise, the amount of particles in the cavity 38 will increase substantially.

The present sensor 12 is designed to determine the amount of metallic particle accumulation within cavity 38, and thereafter convey such information to a remote receiver for appropriate processing. When metallic particles enter the cavity, eddy currents in the particle cause the effective inductance of the first coil 42 to decrease. Consequently, the oscillator 58 will produce the oscillating waveform with an increased frequency. Because eddy currents are a function of material conductivity, the greater the size of a particle or the greater amount of particle accumulation, the greater the change in the oscillating waveform frequency. The detector signal 16 generated is then processed into an rf signal containing encoded information to identify the sensor for transmission to a remote receiver such as the receiver 26. In this regard, each sensor will have a specific identification code for the particular work machine or system into which it is incorporated. Since receiver 26 could pick up other signals from other sensors, or from other work machines in the area, receiver 26 will act as a discriminator and will only receive properly coded signals based upon the identification code of the sensor 12. All other signals will be ignored by receiver 26. In addition, microprocessor 28 could likewise be programmed to discriminate signals received from receiver 26 based upon the identification code of sensor 12, or other sensors. In this scenario, microprocessor 28 can function as a back-up discriminator to receiver 26.

In addition, the present invention compensates for changing inductance due to changing fluid temperature. Because the inductance values of coils 42 and 44 both change in response to temperature, and because the inductance values of each coil are indirectly compared to each other, the present invention is able to distinguish between the changing inductance value due to temperature and those inductance values that are attributed to particle accumulation.

The present sensor 12 may also be periodically calibrated, at will, through the use of a service tool such as a laptop computer which can be coupled to the microprocessor 18 through conventional means. Calibration of the sensor is typically accomplished in order to reprogram the microprocessor 18 to a new or desired sensitivity level based upon the particular application for which the sensor is being utilized. For example, each sensor of the present invention is programmed with a default sensitivity level or predetermined value above which the monitoring system 30 will provide a warning signal to the machine operator and/or to some other remote location for diagnostic and/or prognostic use. Depending upon the particular application and use of the sensor 12, this predetermined sensitivity value or level may have to be re-calibrated. For example, in the situation where the sensor 12 is being used to sense particle accumulation in a final drive assembly such as the assembly 64 illustrated in FIG. 4, the sensitivity level of the sensor 12 will be quite different than if the same sensor is being utilized in a hydraulic system to monitor the condition of a hydraulic pump or other associated hydraulic components. In the case of the final drive assembly 64, since many gears and other wear components are typically associated with a final drive/differential assembly, a higher level of metallic particles will normally be present in the lubricating fluid as compared to a hydraulic system which incorporates a hydraulic pump and other components. In other words, the cavity 38 of sensor 12 will accumulate more metallic particles when the sensor is used in conjunction with the final drive assembly 64 as compared to the accumulation of metallic particles within the cavity 38 when the sensor 12 is used in a typical hydraulic system. In this scenario, a few metallic particles detected in cavity 38 may indicate abnormal wear and impending failure of a major system component such as a hydraulic pump when the sensor 12 is used in a particular hydraulic circuit, whereas the same amount of particle accumulation, or even a much higher level of particle accumulation, within the cavity 38 may be representative of normal operating conditions when the sensor 12 is used in a final drive cavity. As a result, the sensitivity level or the predetermined value above which the monitoring system 30 will trigger a warning signal will be quite different. Recalibration of the sensor 12 may therefore be required depending upon the default value programmed into the microprocessor 18 at the factory. Programming within the microprocessor 18 enables the present sensor to be easily calibrated or re-calibrated, as necessary.

Other operating conditions may likewise dictate recalibration of the sensor 12 in the field. For example, the monitoring system 30 may produce a warning signal to the operator if microprocessor 28 determines that the rate of increase of particle accumulation within the cavity, over time, based upon a comparison of previous stored readings, is above a predetermined rate of increase or value. This means that particles are accumulating within the fluid at such a rate that impending failure of a component is very likely to occur. In this case, the predetermined value associated with the signal would be based upon the slope of the line representing the rate of increase of particles in the fluid over time. Other maps or algorithms could be used and programmed into microprocessor 28 to accomplish this task.

Microprocessor 28 could likewise be an electronic controller or module, which devices are commonly used in association with work machines for accomplishing various tasks. Such controllers or modules 28 may typically include processing means, such as a microcontroller or microprocessor, associated electronic circuitry such as input/output circuitry, analog circuits or programmed logic arrays, as well as associated memory. Microprocessor or controller 28 can therefore be programmed to act as a back-up discriminator as previously discussed, and such microprocessor can be programmed to sense and recognize the appropriate signals indicative of the particle accumulation level within cavity 38 from receiver 26 and, based upon such sensed conditions, provide appropriate output signals to the monitoring system 30 as discussed above. In addition, microprocessor 28 will store and monitor all of the data received from sensor 12 over time and will access and utilize such data in diagnosing or predicting a component or system failure.

It is also recognized that variations to the steps depicted in flow chart 72 could be made without departing from the spirit and scope of the present invention. In particular, steps could be added or some steps could be eliminated. All such variations are intended to be covered by the present invention.

Although there has been illustrated and described a specific structure and a specific method of operation, it is clearly understood that the same is merely for purposes of illustration and that changes and modifications may be readily made to both the construction and method of operation of the sensor system 10 by those skilled in the art without departing from the spirit and scope of the present invention.

Other aspects, objects and advantages of the present invention can be obtained from a study of the drawings, the disclosure and the appended claims.

We claim:

1. A sensor system carried by a work machine for sensing particle accumulation within a fluid contained in a work machine component and transmitting a signal representative of such particle accumulation to a receiver carried by the work machine, said system comprising:

a sensor carried by a work machine positionable relative to a fluid and capable of generating an electrical signal responsive to the particle accumulation within the fluid;

a first microprocessor coupled to said sensor for receiving electrical signals therefrom and for outputting a signal indicative of the particle accumulation in the fluid;

a transmitter coupled to said first microprocessor for processing the signals received from said first microprocessor into rf signals and transmitting said rf signals;

a receiver carried by the work machine and positioned at a location remote from said transmitter for receiving the rf signals from said transmitter and processing said signals back into an electrical signal; and a second microprocessor coupled to said receiver for receiving and storing the electrical signals from said receiver, said electrical signals being indicative of the particle accumulation within the fluid.

2. The sensor system as set forth in claim 1 wherein the sensor, first microprocessor and transmitter are powered by at least one battery carried by a portion of the sensor system.

3. The sensor system as set forth in claim 2 wherein the first microprocessor and transmitter operate alternately in a sleep mode and run mode.

4. The sensor system, as set forth in claim 1, wherein said second microprocessor produces a signal indicative of the particle accumulation in the fluid.

5. The sensor system, as set forth in claim 4, including a monitoring system adapted to receive signals from said second microprocessor and producing a warning signal in response thereto if said signal exceeds a predetermined value.

6. The sensor system, as set forth in claim 5, wherein said predetermined value is based upon a rate of increase of particle accumulation with the fluid.

7. The sensor system, as set forth in claim 5, wherein said sensor can be re-calibrated to change the predetermined value above which a warning signal will be produced by said monitoring system.

8. The sensor system, as set forth in claim 1, wherein said first microprocessor encodes the electrical signals received from said sensor with an identification code unique to said sensor.

9. The sensor system, as set forth in claim 8, wherein said receiver only processes those rf signals encoded with the identification code unique to said sensor.

10. The sensor system as set forth in claim 8 wherein there are a plurality of said sensors carried by the work machine each having a respective and first microprocessor and transmitter.

11. The sensor system as set forth in claim 10 wherein each sensor and respective microprocessor and transmitter are powered by a respective battery.

12. An apparatus carried by a work machine for detecting particles within a fluid contained in a work machine component, comprising:

a housing unit including a cavity, said housing unit carried by a work machine;

a first coil disposed adjacent said cavity to generate electrical signals responsive to the temperature of the fluid, said signal being independent of any particle accumulation within said cavity;

a second coil disposed adjacent said cavity to generate electrical signals responsive to the particle accumulation within said cavity, said electrical signals being representative of particle accumulation within said cavity in response to the change of the inductance of said second coil due to accumulation of particles within said cavity;

a first microprocessor coupled to said first and second coils for receiving electrical signals therefrom, said microprocessor encoding said electrical signals specific to said apparatus;

a transmitter coupled to said first microprocessor for transmitting said encoded signals to a remote location;

a receiver carried by said work machine and disposed at said remote location for discriminating among a plurality of signals in order to identify and decode signals specific to said apparatus; and a second microprocessor coupled to said receiver for receiving signals from said receiver and producing a signal indicative of the particle accumulation within said cavity.

13. An apparatus, as set forth in claim 12, wherein the electrical signals representative of the identifying accumulation with said cavity are encoded with identifying information representative of said apparatus.

14. An apparatus carried by a work machine for detecting particles within a fluid contained in a work machine component comprising:

a housing adapted for at least partial placement in a fluid system and including a cavity, said housing being carried by a work machine;

a magnet disposed adjacent to said cavity and adapted to attract and contain particles within said cavity;

a first coil wound about the outer surface of said cavity, the inductance of said first coil being responsive to the particle accumulation within said cavity;

a second coil spaced from said first coil, the inductance of said second coil being responsive to the temperature of the fluid and being independent of any particle accumulation within said cavity;

a first microprocessor coupled to said first and second coils adapted to receive electrical signals therefrom, said first microprocessor determining the particle accumulation within said cavity and producing a detecting signal representative thereof;

an rf transmitter coupled to said first microprocessor for processing the detecting signal into an rf signal;

a first antenna coupled to said rf transmitter for transmitting the rf signal from said transmitter;

a second antenna carried by the work machine and positioned at the remote location from the first antenna for receiving the rf signal;

an rf receiver coupled to said second antenna for receiving and processing the rf signal into electrical signals, said electrical signals being representative of the particle accumulation within said cavity; and a second microprocessor carried by the work machine and coupled to said rf receiver and adapted to receive electrical signals therefrom, said second microprocessor storing and monitoring the particle accumulation data represented by the signals received from said rf receiver.

15. The apparatus, as set forth in claim 14, wherein said housing includes first and second members, one of said members including said cavity and being engageable with said other member.

16. The apparatus, as set forth in claim 14, including a monitoring system adapted to receive a signal from said second microprocessor, said monitoring system producing a warning signal in response to the signal received from said second microprocessor if said signal exceeds a predetermined value.

17. The apparatus, as set forth in claim 14, wherein said first microprocessor and said rf transmitter are located within said housing.

18. The apparatus, as set forth in claim 14, wherein the signals representative of particle accumulation within said cavity are encoded with identifying information representative of said detecting apparatus.

19. The apparatus, as set forth in claim 18, wherein the electrical signal transmitted from said rf receiver to said second microprocessor includes the identifying information representative of said detecting apparatus.

20. The apparatus, as set forth in claim 17, including an oscillator selectively coupled to the first and second coils for producing an oscillating waveform, wherein the frequency of the oscillating waveform is a function of the induction of one of said first and second coils.

21. The apparatus, as set forth in claim 20, including a multiplexer adapted to select one coil to energize at a given time.

22. The apparatus, as set forth in claim 21, wherein the oscillator produces an oscillating waveform having a series of pulses the frequency of which is a function of the one energized coil inductance.

23. A method for detecting particles within a fluid contained within a work machine component comprising the following steps:

providing a sensor capable of detecting particle accumulation within a fluid in a work machine component and providing a signal indicative of said particle accumulation;

generating a signal indicative of the particle accumulation within the fluid;

encoding said signal with identifying information unique to said sensor;

converting said signal into an rf signal and transmitting said rf signal to a remote location on the work machine;

receiving said rf signal at said remote location;

decoding said rf signal based upon said identifying information unique to said sensor; and reading and storing said decoded signal at said remote location wherein the particle accumulation within the fluid is monitored.

24. The method as set forth in claim 23 including providing at least one battery for powering the signal generation, the signal encoding and the rf signal transmitting steps.

25. The method as set forth in claim 23 wherein the signal generating, signal encoding and rf signal transmitting steps alternate between a run mode and a sleep mode.

* * * * *